United States Patent
Frasch et al.

(10) Patent No.: US 9,958,524 B2
(45) Date of Patent: May 1, 2018

(54) PROBE CALIBRATION DEVICES AND METHODS

(71) Applicant: The Boeing Company, Chicago, IL (US)

(72) Inventors: Lydell L. Frasch, Dardenne Prairie, MO (US); Nathaniel P. Roman, Ballwin, MO (US)

(73) Assignee: THE BOEING COMPANY, Chicago, IL (US)

( * ) Notice: Subject to any disclaimer, the term of this patent is extended or adjusted under 35 U.S.C. 154(b) by 207 days.

(21) Appl. No.: 14/737,229

(22) Filed: Jun. 11, 2015

(65) Prior Publication Data

US 2017/0082719 A1    Mar. 23, 2017

(51) Int. Cl.
| | |
|---|---|
| G01R 35/00 | (2006.01) |
| G01R 27/06 | (2006.01) |
| H01P 5/08 | (2006.01) |
| G01R 3/00 | (2006.01) |
| G01R 23/165 | (2006.01) |
| G01B 21/04 | (2006.01) |
| G01B 7/06 | (2006.01) |

(Continued)

(52) U.S. Cl.
CPC .......... *G01R 35/007* (2013.01); *G01B 7/085* (2013.01); *G01B 21/042* (2013.01); *G01R 3/00* (2013.01); *G01R 23/165* (2013.01); *G01R 27/06* (2013.01); *H01P 5/082* (2013.01); *G01N 22/00* (2013.01); *G01R 23/07* (2013.01)

(58) Field of Classification Search
USPC .................. 324/601, 754.01, 754.11; 702/85
See application file for complete search history.

(56) References Cited

U.S. PATENT DOCUMENTS

| | | | | |
|---|---|---|---|---|
| 3,504,308 A | * | 3/1970 | Mayerhofer | H01J 23/24 315/3.5 |
| 3,919,666 A | * | 11/1975 | Posner | H03B 9/145 331/107 DP |

(Continued)

FOREIGN PATENT DOCUMENTS

| | | |
|---|---|---|
| DE | 1792402 A1 | 11/1971 |
| EP | 2620741 A1 | 7/2013 |

OTHER PUBLICATIONS

Extended European Search Report for EP Application No. 16174054.3-1568 from the European Patent Office dated Oct. 19, 2016, 8 pages.

(Continued)

*Primary Examiner* — Melissa Koval
*Assistant Examiner* — Nasima Monsur
(74) *Attorney, Agent, or Firm* — Toler Law Group, P.C.

(57) ABSTRACT

A probe calibration device that includes a first offset element having a substantially rectangular first aperture. The probe calibration device includes a tuned pass element disposed adjacent to the first offset element. The tuned pass element has a non-rectangular second aperture. The probe calibration device includes a second offset element disposed adjacent to the tuned pass element and on a side opposite the first offset element. The second offset element has a substantially rectangular third aperture. The probe calibration device includes a backing element disposed adjacent to the second offset element. The first offset element, the tuned pass element, the second offset element and the backing element form a cavity.

20 Claims, 7 Drawing Sheets

(51) Int. Cl.
*G01N 22/00* (2006.01)
*G01R 23/07* (2006.01)

(56) References Cited

U.S. PATENT DOCUMENTS

| | | | | |
|---|---|---|---|---|
| 3,999,263 | A * | 12/1976 | Marshall | H01J 9/02 445/36 |
| 4,996,492 | A * | 2/1991 | Anderson | G01B 7/13 324/662 |
| 5,018,259 | A * | 5/1991 | Wildman | A61C 7/12 216/33 |
| 6,184,694 | B1 | 2/2001 | Anderson et al. | |
| 6,297,648 | B1 | 10/2001 | Lunden | |
| 6,496,018 | B1 | 12/2002 | Nagata et al. | |
| 7,173,435 | B1 | 2/2007 | Fay et al. | |
| 7,898,265 | B2 | 3/2011 | Takeuchi et al. | |
| 8,060,232 | B2 * | 11/2011 | Kuntz | G01M 7/025 700/108 |
| 2005/0156606 | A1 | 7/2005 | Sergoyan et al. | |
| 2005/0265915 | A1 * | 12/2005 | Tonkovich | B01J 19/0093 423/584 |
| 2007/0297868 | A1 * | 12/2007 | Wickham | B23B 31/026 408/127 |
| 2009/0140751 | A1 | 6/2009 | Takeuchi et al. | |
| 2013/0038524 | A1 * | 2/2013 | Otsuki | G06F 3/0425 345/156 |

OTHER PUBLICATIONS

"Waveguide Handbook", New York Dover Publications, Inc., New York, NY, <https://ia800308.us.archive.org/24/items/WaveguideHandbook/Marcuvitz-WaveguideHandbook_text.pdf>, 1965, 459 pages.

* cited by examiner

PROBE CALIBRATION DEVICES AND METHODS

STATEMENT REGARDING FEDERALLY SPONSORED RESEARCH OR DEVELOPMENT

This invention was made with Government support under contract F33615-03-D-5204 awarded by the Department of Defense. The government has certain rights in the invention.

FIELD OF THE DISCLOSURE

The disclosure generally relates to electrical measuring equipment and methods. In particular, the disclosure relates to microwave equipment and methods for measuring the impedance of conductive materials and thickness of dielectric topcoats.

BACKGROUND

An impedance/conductivity cavity probe can be formed using a rectangular waveguide. A closed rectangular cavity has six metal walls with a small iris located in the center of one of the walls. Electromagnetic energy (e.g., radio frequency (RF) or microwave energy) may be coupled into and out of the cavity via the iris. The iris will couple energy at a particular frequency (e.g., a resonant frequency) into the cavity while not coupling energy at frequencies other than the particular frequency. Thus, as energy is fed to the impedance/conductivity cavity probe over a band of frequencies, most of the energy will be returned except at the resonant frequency. If one plots the returned energy as a function of frequency, a sharp null will be located at the resonant frequency.

An open-ended cavity probe may be formed by removing one of the six walls of the closed rectangular cavity, resulting in a cavity with five walls (e.g., an open-ended cavity). The open-ended cavity probe may be used to measure properties of a sample by placing the sample proximate to the open end of the open-ended cavity, thereby effectively closing the open-ended cavity.

In some examples, the sample may be a conductive material. Closing the open-ended cavity probe with the conductive material sample may result in a null at the resonant frequency of the chamber including one wall corresponding to the sample. For a sample with conductivity close to that of a metallic surface, the null may have the same depth as if the original metal wall (e.g., of the closed rectangular cavity) was still in place. If the material is less conductive than a metallic surface, then the null may still be located at the resonant frequency, but it may not be as deep. As the material becomes less conductive, the null may become shallower until it completely disappears.

The open-ended cavity probe can be used to measure the conductivity of a given sample based on a relationship between the null depth and conductivity. The open-ended cavity probe may be calibrated by measuring probe responses to conductive material samples, referred to as materials standards, and establishing a relationship between the probe responses (e.g., null depth of the probe responses) and the known constitutive properties of the materials standards (e.g., conductivity).

In other examples, the sample may include a conductive material coated by a non-conductive (e.g. dielectric) layer. The open-ended cavity probe may still be used to measure conductivity/impedance of samples that include a thin dielectric topcoat, although a different calibration/relationship needs to be established than when the samples do not include a dielectric topcoat. For example, the null depth returned by the open-ended cavity probe when closed by a sample including a conductive material coated by a non-conductive layer may still be related to the conductivity of the sample (as with a purely conductive material), but the relationship between null depth and conductivity may be modified somewhat by the presence of the dielectric topcoat. In addition, the null measured when the open-ended cavity probe is closed by a sample including a conductive material coated by a non-conductive layer may no longer present at the same resonant frequency as when the sample is a purely conductive material. The amount of shift may be influenced by the thickness of the dielectric topcoat. A cavity probe is typically calibrated to measure conductivity/impedance of samples that include a dielectric topcoat using different materials standards (e.g., samples) formed of different conductive materials in combination with two thickness of a dielectric for the purposes of performing the calibration. However, this can be problematic in a field or mobile environment as the samples can get damaged or lost. In addition, the materials of the samples can degrade with time, and it may be problematic to make materials consistently.

SUMMARY

In a particular embodiment, a probe calibration device includes a first offset element having a substantially rectangular first aperture. The probe calibration device includes a tuned pass element disposed adjacent to the first offset element. The tuned pass element has a non-rectangular second aperture. The probe calibration device includes a second offset element disposed adjacent to the tuned pass element and on a side opposite the first offset element. The second offset element has a substantially rectangular third aperture. The probe calibration device includes a backing element disposed adjacent to the second offset element. The first offset element, the tuned pass element, the second offset element and the backing element form a cavity.

In a particular embodiment, a method of calibrating a probe includes applying energy to a probe coupled to a calibration device. The calibration device includes a first offset element having a substantially rectangular first aperture. The calibration device includes a tuned pass element disposed adjacent to the first offset element. The tuned pass element has a non-rectangular second aperture. The calibration device includes a second offset element disposed adjacent to the tuned pass element and on a side opposite the first offset element. The second offset element has a substantially rectangular third aperture. The calibration device includes a backing element disposed adjacent to the second offset element. The first offset element, the tuned pass element, the second offset element and the backing element form a cavity. The method further includes measuring electromagnetic energy returned by the probe in response to application of the energy to the probe when the probe is coupled to the calibration device.

In a particular embodiment, a method of manufacturing a probe calibration device includes obtaining a first offset element having a substantially rectangular first aperture. The method includes obtaining a tuned pass element including a non-rectangular second aperture. The method includes obtaining a second offset element having a substantially rectangular third aperture. The method includes obtaining a backing element. The method includes assembling the first offset element, the tuned pass element, the second offset element, and the backing element such that the tuned pass element is adjacent to the first offset element and the second offset element and such that the backing element is disposed adjacent to the second offset element. The first offset element, the tuned pass element, the second offset element and the backing element form a cavity.

The features, functions, and advantages that have been described can be achieved independently in various embodiments or may be combined in yet other embodiments, further details of which are disclosed with reference to the following description and drawings.

DETAILED DESCRIPTION

Particular embodiments of the present disclosure are described below with reference to the drawings. In the description, common features are designated by common reference numbers throughout the drawings.

Figure 1:
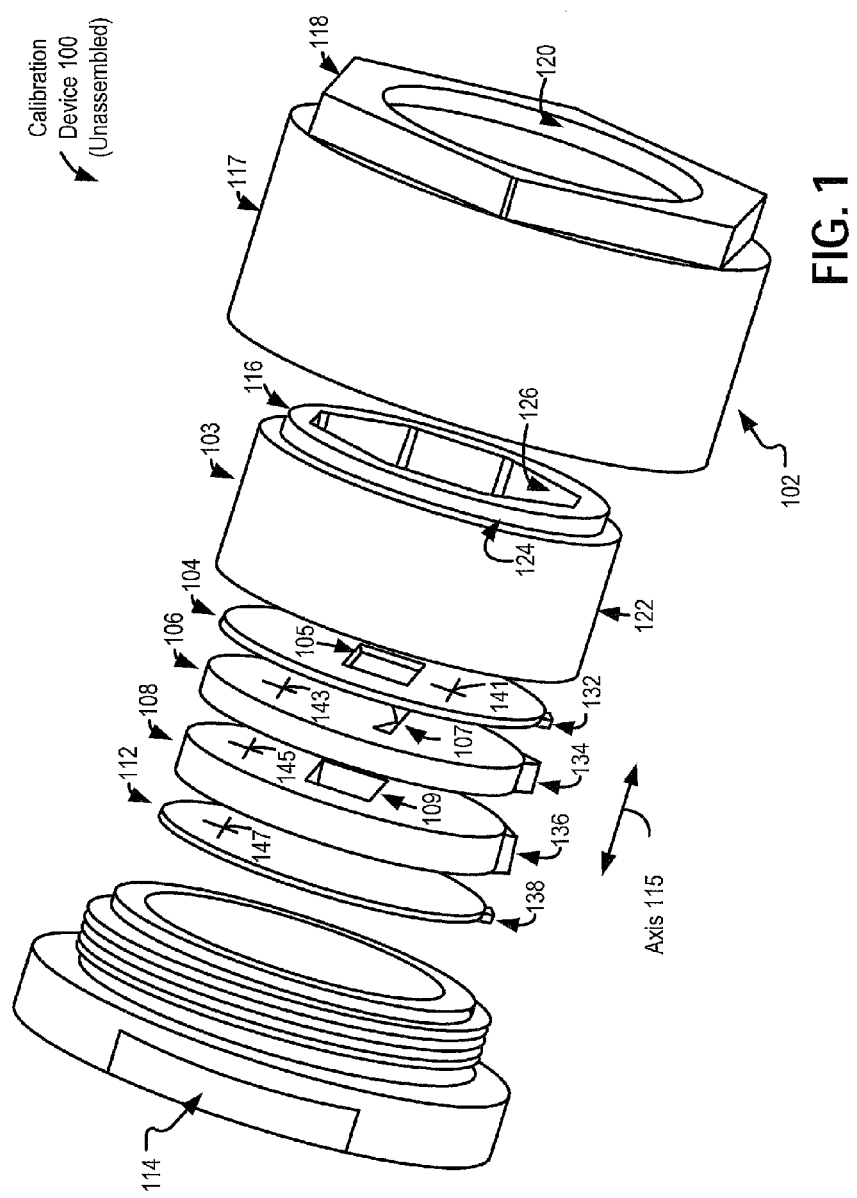
FIG. 1 is a perspective view of an unassembled particular embodiment of a probe calibration device.
Figure 2:
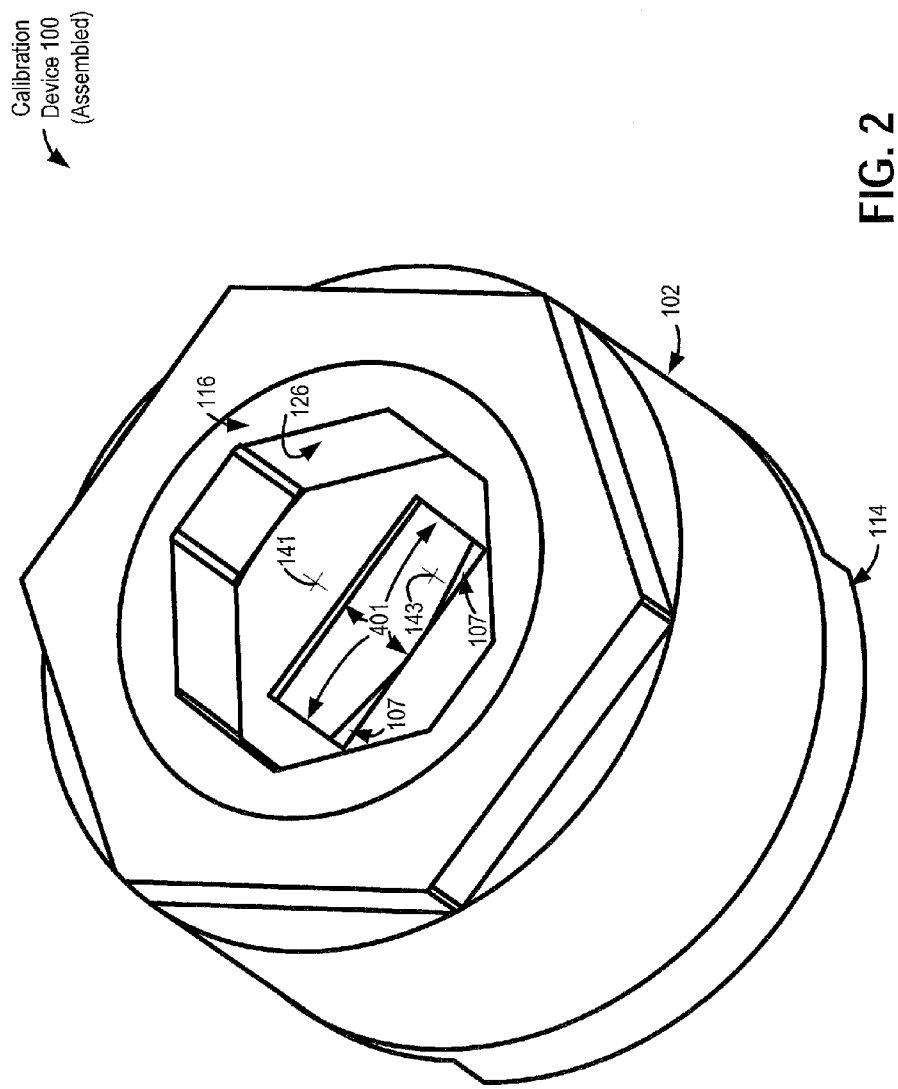
FIG. 2 is a perspective view of the probe calibration device of FIG. 1 as assembled.

Referring to FIG. 1, a perspective view of an unassembled embodiment of a probe calibration device 100 is depicted. Referring to FIG. 2, a perspective view of the probe calibration device 100 of FIG. 1 after assembly is depicted. The probe calibration device 100 may be configured to calibrate a probe, such as an open-ended rectangular waveguide cavity probe, used to perform materials composition testing. The probe may be used to measure conductivity or impedance of materials including a conductive material at least partially coated with a dielectric material.

The probe calibration device 100 may include a first offset element 104, a tuned pass element 106, a second offset element 108, and a backing element 112. The first offset element 104, the tuned pass element 106, the second offset element 108, the backing element 112, or a combination thereof, may be formed of or include metal. Dimensions of the first offset element 104, the tuned pass element 106, the second offset element 108, or a combination thereof, may be selected such that the probe calibration device 100 mimics a particular materials standard (e.g., has an electromagnetic response corresponding to an electromagnetic response of the particular materials standard) when the probe calibration device 100 is used to test/calibrate a probe, as described in more detail below.

In some implementations, the first offset element 104, the tuned pass element 106, the second offset element 108, the backing element 112, or a combination thereof, may be substantially circularly cylindrically shaped elements. In other implementations, the first offset element 104, the tuned pass element 106, the second offset element 108, the backing element 112, or a combination thereof, may have a non-circular cylindrical geometry.

The first offset element 104 may include a substantially rectangular aperture 105 (e.g., a "first aperture"). In some implementations, the first aperture 105 may be centered in the first offset element 104. The second offset element 108 may include a substantially rectangular aperture 109 (e.g., a "third aperture"). In some implementations, the third aperture 109 may be centered in the second offset element 112.

Figure 5:
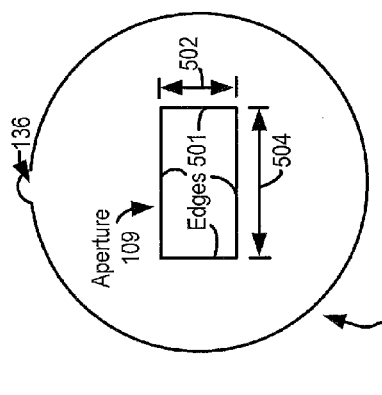
FIG. 5 illustrates a top view of a particular embodiment of a second offset element of the probe calibration device of FIGS. 1-3.
Figure 4:
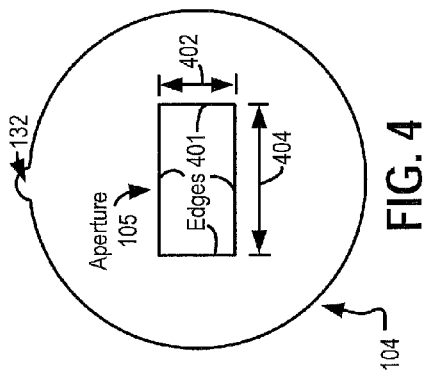
FIG. 4 illustrates a top view of a particular embodiment of a first offset element of the probe calibration device of FIGS. 1-3.

In some implementations, a cross-sectional shape of the first aperture 105 and a cross-sectional shape of the third aperture 109 may have substantially same dimensions. For example, FIGS. 4 and 5 may illustrate top views of the first offset element 104 and the second offset element 108, respectively, of FIG. 1. As illustrated in FIGS. 4 and 5, the first aperture 105 may have a height 402 and a length 404, and the third aperture 109 may have a height 502 and a length 504. In some implementations, the length 404 of the first aperture 105 is substantially the same as the length 504 of the third aperture 109, the height 402 of the first aperture 105 is substantially the same as the height 502 of the third aperture 109, or both.

Figure 3:
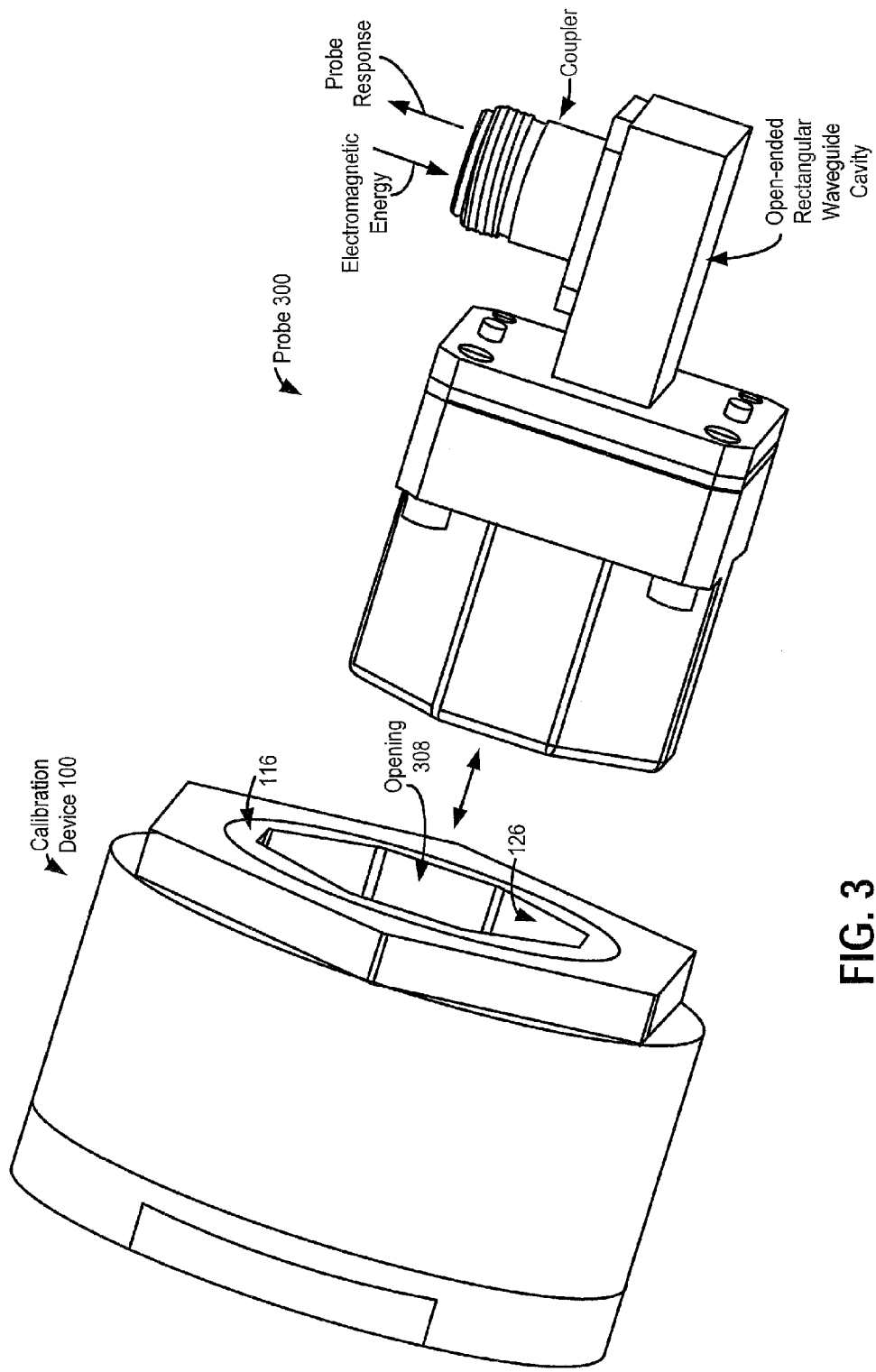
FIG. 3 illustrates the probe calibration device 100 of FIG. 1 in proximity to a particular embodiment of an open-ended rectangular waveguide probe.

A cross section of the first aperture 105, a cross-section of the third aperture 109, or both, may correspond to dimensions of a cross-section of an interior cavity of a cavity probe that the probe calibration device 100 may be used to calibrate, such as the open-ended rectangular waveguide probe 300 of FIG. 3. In some examples, the first aperture 105, the third aperture 109, or both, may have dimensions corresponding to standard commercially available rectangular waveguide band interior dimensions having commercial broad wall and short wall dimensions.

In some implementations, the first offset element 104 and the second offset element 108 have different thicknesses. For example, in some embodiments, the second offset element 108 may be thicker than the first offset element 104.

The tuned pass element 106 may include a non-rectangular aperture 107 (e.g., a "second aperture"). In some implementations, a cross-sectional shape of the second aperture 107 may correspond to a rooftop shape. For example, FIG. 6 may illustrate a top view of the tuned pass element 106 and the second aperture 107 of FIG. 1, and the cross-sectional shape of the second aperture 107 may correspond to two overlapping (e.g., partially overlapping) triangles 604 (e.g., substantially congruent right triangles). For example, the triangles 604 may partially overlap at overlapping region 612. A length 605 of the second aperture 107 may correspond to the length 404 of the first aperture 105 of FIGS. 1 and 4 and/or may correspond to the length 504 of the third aperture 109 of FIGS. 1 and 5. A height 603 of the second aperture 107 of FIGS. 1 and 6 may be less than the height 402 of the first aperture 105 of FIGS. 1 and 4 and/or may be less than the height 502 of the third aperture 109 of FIGS. 1 and 5.

The probe calibration device 100 of FIGS. 1 and 2 may further include a first outer body section 102, a second outer body section 114, and a guide section 103. The first outer body section 102 may be configured to removably couple to the second outer body section 114 (e.g., using threads of the first outer body section 102 and the second outer body section 114). When coupled together, the first outer body section 102 and the second outer body section 114 may house and/or at least partially enclose internal components, such as the guide section 103, the first offset element 104, the tuned pass element 106, the second offset element 108, and/or the backing element 112. The guide section 103 may be configured (e.g., shaped) to align the internal components and to guide and orient the cavity probe so that the cavity probe properly engages the probe calibration device 100. Differently shaped outer housing elements and guide section may be used to accommodate differently shaped cavity probes.

The first outer body section 102 may include a body section 117 and a protrusion section 118. The guide section 103 may include a body section 122 and a protrusion section 116. The first outer body section 102 may be configured and dimensioned to receive the guide section 103. For example, the first outer body section 102 may include a cavity or hollow region of the body section 117. The cavity or hollow region of the body section 117 may be dimensioned such that dimensions of a cross-section of an inner surface defining the cavity or hollow region of the body section 117 correspond to dimensions of a cross-section of the outer surface of the body section 122 of the guide section 103. Additionally or alternatively, dimensions of a cross-section of an inner surface 120 of the protrusion 118 of the first outer body section 102 may correspond to dimensions of a cross-section of an outer surface 124 of the protrusion 116 of the guide section 103. Thus, the guide section 103 may be configured to slide into the first outer body section 102 such that an outer surface of the body section 122 is proximate to an inner surface of the body section 117, and such that the outer surface 124 is proximate to the inner surface 120.

The protrusion 116 of the guide section 103 may include an inner surface 126 dimensioned to slidingly receive a body of a probe. For example, FIG. 3 illustrates an example of an open-ended rectangular-waveguide cavity probe 300 positioned relative to the probe calibration device 100 of FIG. 2. As the cavity probe 300 of FIG. 3 and the probe calibration device 100 approach along the line indicated by the double-arrow, the cavity probe 300 may be seated within opening 308, with a tip of the probe 300 abutting a surface of the first offset element 104 of FIGS. 1 and 2. When seated in the opening 308, the open end of the open-ended rectangular waveguide of the cavity probe 300 is aligned (e.g., along the axis or the direction described below) with the first aperture 105 and the third aperture 109. Aligning the open end of the open-ended rectangular waveguide of the cavity probe 300 of FIG. 3 with the first aperture 105 of FIG. 1 allows for smooth transitions between the cavity probe 300 and the probe calibration device 100 of FIGS. 1 and 2.

Figure 8:
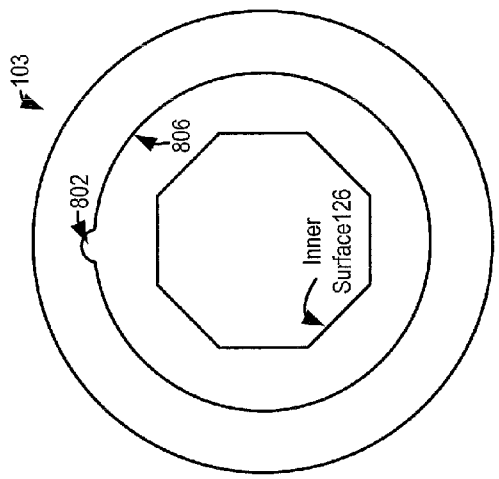
FIG. 8 illustrates a bottom view of a particular embodiment of a guide section of the probe calibration device of FIGS. 1-3.
Figure 7:
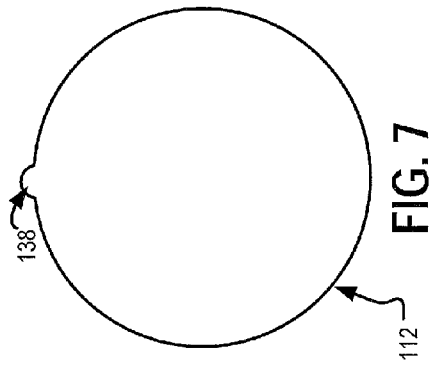
FIG. 7 illustrates a top view of a particular embodiment of a backing element of the probe calibration device of FIGS. 1-3.

FIG. 8 illustrates a bottom view of the guide section 103 of FIG. 1. The guide section 103 may include a slot 802 of FIG. 8 along an interior surface 806 of the body section 122 of FIG. 1. The first offset element 104 of FIGS. 1 and 4 may include a protrusion 132, the tuned pass element 106 of FIGS. 1 and 6 may include a protrusion 134, the second offset element 108 of FIGS. 1 and 5 may include a protrusion 136, and the backing element 112 of FIGS. 1 and 7 may include a protrusion 138. The protrusions 132, 134, 136, and 138 may be dimensioned and configured to fit in the slot 802 of FIG. 8 along the interior surface of the body section 122 of FIG. 1. The protrusions 132, 134, 136, and 138 may engage with the slot 802 of FIG. 8 to orient the first offset element 104 of FIGS. 1 and 4, the tuned pass element 106 of FIGS. 1 and 6, and the second offset element 108 of FIGS. 1 and 5 in a particular orientation to align the first aperture 105, the second aperture 107, and/or the third aperture 109 in a particular alignment with each other and/or in a particular alignment with a cavity of a cavity probe as described above.

For example, in some implementations, the protrusion 132 of the first offset element 104 of FIGS. 1 and 4 and the protrusion 136 of the second offset element 108 of FIGS. 1 and 5 may engage with the slot 802 of FIG. 8 along the interior surface 806 of the guide section 103 to align edges of the first aperture 105 of FIGS. 1 and 4 and edges of the third aperture 109 of FIGS. 1 and 5 along an axis or a direction. In some examples, the axis or the direction may correspond to an axis or a direction normal to a plane parallel to a face (e.g., face 141) of the first offset element 104, to a plane parallel to a face (e.g., face 143) of the tuned pass element 106, to a plane parallel to a face (e.g., face 145) of the second offset element 108, to a plane parallel to a face (e.g., face 147) of the backing element 112, or to a plurality of the planes. In some examples, the axis or the direction may be parallel to axis 115 of FIG. 1. In some examples, the axis or the direction may be parallel to a longitudinal axis of a cavity of the probe 300 of FIG. 3. In some of these implementations, cross-sectional shapes of the first aperture 105 and the third aperture 109 may have substantially same dimensions as described above, and when the device 100 is assembled, edges of the first aperture 105 and edges of the third aperture 109 may be aligned along the axis or the direction described above. To illustrate, with reference to FIGS. 4 and 5, when the probe calibration device 100 of FIGS. 1 and 2 is assembled, edges 401 of FIG. 4 of the first aperture 105 may be aligned along the axis or the direction described above with edges 501 of FIG. 5 of the third aperture 109.

Figure 6:
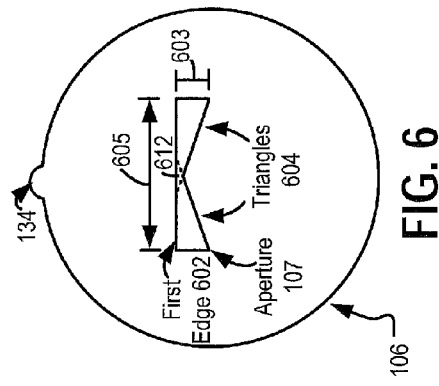
FIG. 6 illustrates a top view of a particular embodiment of a tuned pass element of the probe calibration device of FIGS. 1-3.

Additionally or alternatively, in some implementations, the protrusion 132 of FIGS. 1 and 4, the protrusion 134 of FIGS. 1 and 6, and/or the protrusion 136 of FIGS. 1 and 5 may engage with the slot 802 of FIG. 8 along the interior surface 806 of the guide section 103 to align, along the axis or the direction described above, at least a portion of one or more edges of the second aperture 107 with at least a portion of one or more edges of the first aperture 105 and/or to align, along the axis or the direction described above, at least a portion of one or more edges of the second aperture 107 with at least a portion of one or more edges of the third aperture 109. To illustrate, with reference to FIGS. 4 and 6, when the probe calibration device 100 of FIG. 1 is assembled, an upper edge of the edges 401 of FIG. 4 of the first aperture 105 may be aligned along the axis or the direction described above with a first edge 602 of FIG. 6 of the second aperture 107. Additionally or alternatively, with reference to FIGS. 5 and 6, when the probe calibration device 100 of FIG. 1 is assembled, an upper edge of the edges 501 of FIG. 5 of the third aperture 109 may be aligned along the axis or the direction described above with the first edge 602 of FIG. 6 of the second aperture 107.

Figure 9B:
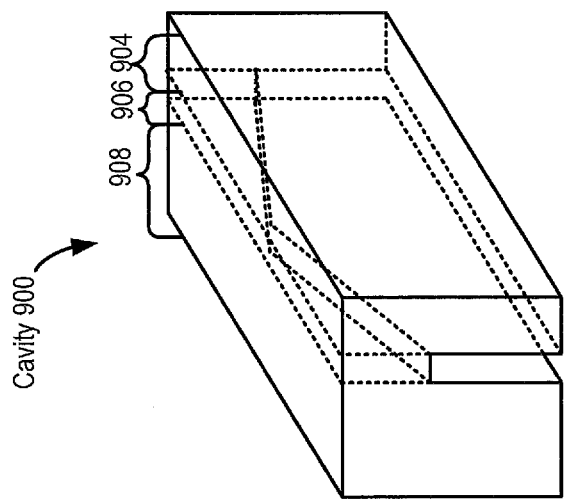
FIG. 9B illustrates a perspective view of the unenclosed cavity of FIG. 9A.
Figure 9A:
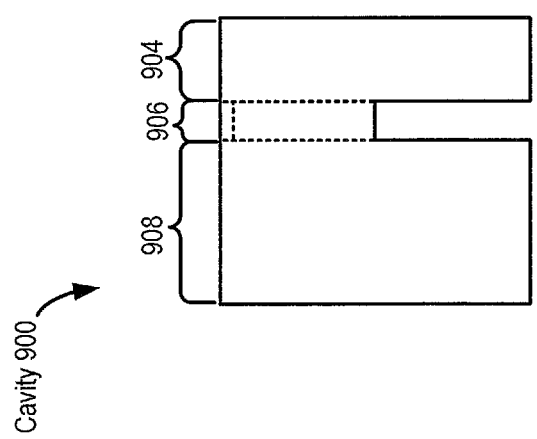
FIG. 9A illustrates a side view of an unenclosed cavity formed by apertures of the first offset element of FIG. 4, the second offset element of FIG. 5, and the tuned pass element of FIG. 6.

When the probe calibration device 100 of FIGS. 1 and 2 is assembled, the first aperture 105, the second aperture 107, the third aperture 109, and the backing element 112 may define a cavity. For example, FIGS. 9A and 9B illustrate a side view and a perspective view, respectively, of a cavity 900 formed by the first aperture 105 of FIG. 1, the second aperture 107, and the third aperture 109. The cavity 900 of FIGS. 9A and 9B may include a first portion 904 defined by the first offset element 104 of FIG. 1 (e.g., corresponding to an unenclosed volume of the first aperture 105), a second portion 906 of FIGS. 9A and 9B defined by the tuned pass element 106 of FIG. 1 (e.g., corresponding to an unenclosed volume of the second aperture 107), and a third portion 908 of FIGS. 9A and 9B defined by the second offset element 108 of FIG. 1 (e.g., corresponding to an unenclosed volume of the third aperture 109). As described below, the cavity 900 of FIGS. 9A and 9B may be dimensioned, such as by using particularly dimensioned components of the probe calibration device 100 of FIGS. 1 and 2, to cause the probe calibration device 100 to mimic particular materials standards having a conductive material backing and a dielectric topcoat and known constitutive properties (e.g., a known conductivity).

For example, dimensions of the tuned pass element 106, the first offset element 104, the second offset element 108, the backing element 112, or a combination thereof, may be selected to control properties of an electromagnetic response measured by a probe (e.g., a probe response), such as the open-ended waveguide probe 300 illustrated in FIG. 3, when the probe calibration device 100 is coupled to the probe 300 and tested. The dimensions may include thicknesses of the first offset element 104 of FIG. 1, the tuned pass element 106, the second offset element 108, the backing element 108, or a combination thereof. The dimensions may also or alternatively include a shape or geometry of the second aperture 107 and/or a cross-sectional area of the second aperture 107. The properties of the electromagnetic response may include a frequency of a null (e.g., corresponding to a resonant frequency) or a magnitude of the response at the resonant frequency. The resonant frequency may be that of a dominant mode or of a higher-order propagating mode.

In some examples, thicknesses of the first offset element 104 and/or the second offset element 108 may be selected to control a location of a null, such as corresponding to a resonant frequency, of the probe response. For example, a resonant frequency measured by the probe 300 of FIG. 3 may be directly or inversely related to thicknesses of the first and second offset elements 104 and 108 of FIG. 1. For example, increasing thicknesses of the first offset element 104 and/or the second offset element 108 may reduce a frequency of a null. As another example, a resonant frequency measured by the probe 300 of FIG. 3 may be directly or inversely related to thickness of the first offset element 104. For example, increasing a thickness of the first offset element while keeping a thickness of the second offset element constant may reduce a frequency of a null. The thicknesses of the first offset element 104 and/or the second offset element 108 may be selected to control a location of a null of the probe response measured using the probe calibration device 100 such that the location of the null corresponds to the location of a null returned using a materials standard having a conductive backing with a particular top layer coat thickness and known constitutive properties. The resonant frequency of the probe response measured using the probe calibration device 100 may be used to calibrate the probe by providing a relationship between the measured resonant frequency and the constitutive properties (e.g., the conductivity) of the materials standard, such as having the conductive backing with the particular dielectric topcoat thickness, that the probe calibration device 100 mimics.

In some examples, a cross-sectional area of the second aperture 107, a geometry of the second aperture 107, and/or a thickness of the second offset element 108 may be selected to control a magnitude of the null of a probe response. For example, a magnitude of the null measured by the probe 300 of FIG. 3 may be directly or inversely related to the cross-sectional area of the second aperture 107 of FIG. 1 and/or a thickness of the second offset element 108. For example, increasing a cross-sectional area of the second aperture 107 and increasing a thickness of the second offset element 108 may increase or reduce a magnitude of a null. As another example, decreasing a cross-sectional area of the second aperture 107 and increasing a thickness of the second offset element 108 may increase or reduce a magnitude of a null. As another example, increasing a cross-sectional area of the second aperture 107 and decreasing a thickness of the second offset element 108 may increase or reduce a magnitude of a null. As another example, decreasing a cross-sectional area of the second aperture 107 and decreasing a thickness of the second offset element 108 may increase or reduce a magnitude of a null. The magnitude of the null of the probe response measured using the probe calibration device 100 may be used to calibrate the probe 300 of FIG. 3 by providing a relationship between the measured null magnitude and the constitutive properties (e.g., the conductivity) of the materials standard, such as having the conductive backing with the particular dielectric topcoat thickness, that the probe calibration device 100 mimics.

Thus, the probe calibration device 100 may be configured using particular components as described above to mimic an electromagnetic response of a particular materials standard having a conductive backing with a particular dielectric topcoat thickness and known constitutive properties. Characteristics, such as resonant frequency and/or null magnitude, of the probe response measured using the probe calibration device 100 can be used to calibrate the probe by providing a relation between the characteristics and a sample having the conductive backing with the particular dielectric topcoat thickness and the constitutive properties.

Figure 10:
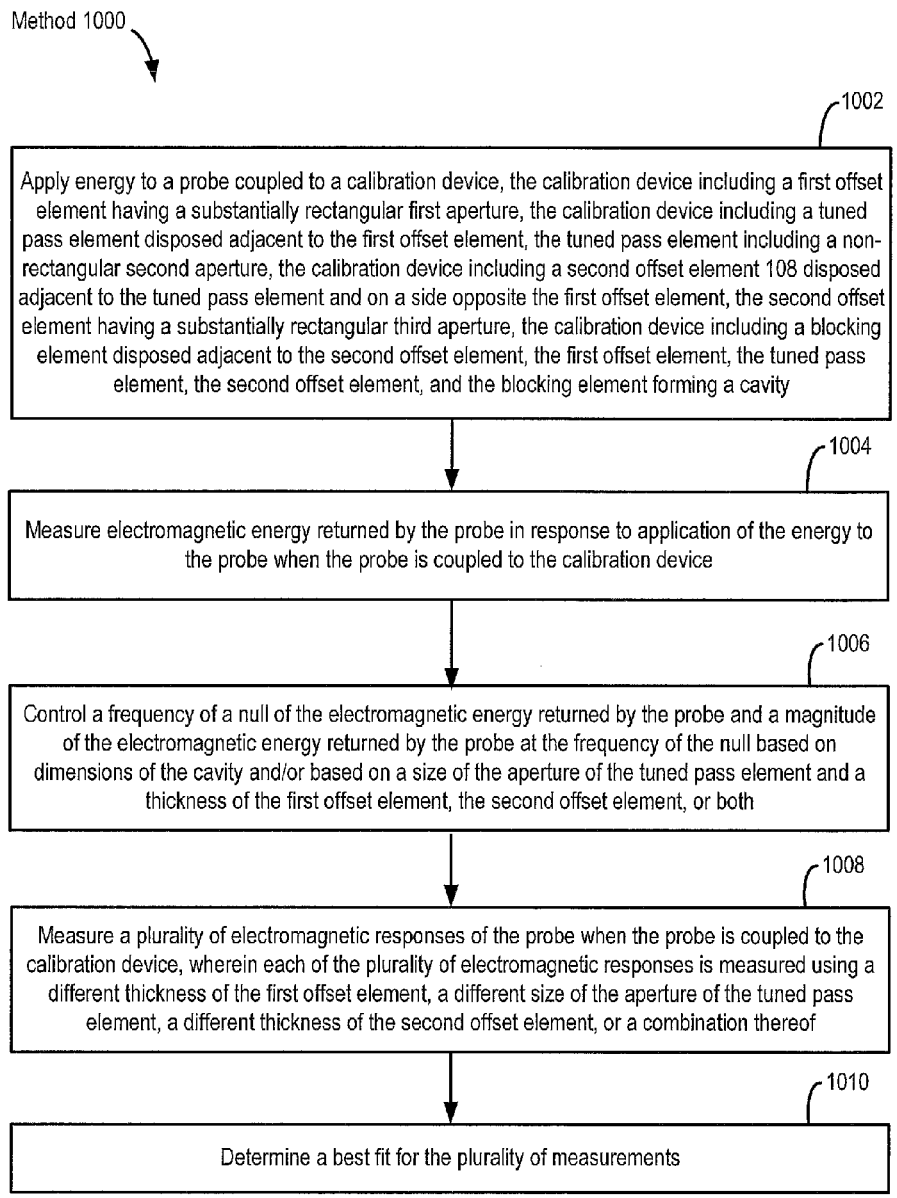
FIG. 10 is a flow chart of a method of calibrating a probe.

Referring to FIG. 10, a flow chart of a particular embodiment of a method 1000 of calibrating a probe is depicted. The method 1000 includes, at 1002, applying energy to a probe coupled to a calibration device. The probe may include an open-ended waveguide probe, such as the open-ended rectangular waveguide cavity probe 300 of FIG. 3. The calibration device may be coupled to the probe as described above with reference to FIG. 3, and the probe may apply electromagnetic energy. The electromagnetic energy applied to the probe may include a band of frequencies.

The calibration device may correspond to the probe calibration device 100 of FIGS. 1 and 2. The calibration device may include a first offset element 104 having a substantially rectangular first aperture 105 as described above with reference to FIGS. 1, 2, and 4. The calibration device may include a tuned pass element 106 disposed adjacent to the first offset element 104 as described above. The tuned pass element 106 may include a non-rectangular second aperture 107 as described above with reference to FIGS. 1, 2, and 6. The calibration device may further include a second offset element 108 disposed adjacent to the tuned pass element 106 and on a side opposite the first offset element 104. The second offset element 108 may have a substantially rectangular third aperture 109 as described above with reference to FIGS. 1, 2, and 5. The calibration device may further include a backing element 112 disposed adjacent to the second offset element 108 as described above with reference to FIGS. 1, 2, and 7. The first offset element 104, the tuned pass element 106, the second offset element 108 and the backing element 112 form a cavity, such as the cavity 900 as described above with reference to FIGS. 9A and 9B. The method 1000 further includes, at 1004, measuring electromagnetic energy returned by the probe in response to application of the energy to the probe when the probe is coupled to the calibration device. The electromagnetic energy returned by the probe may be measured using a vector network analyzer. The electromagnetic energy returned by the probe may include a null at a particular frequency. The particular frequency may correspond to a measured resonant frequency of a cavity formed by closing the open-ended rectangular waveguide cavity using a materials standard including a conductive layer and a dielectric topcoat and having known constitutive properties. Additionally, the electromagnetic energy returned by the probe may include a particular magnitude at the particular frequency. The particular magnitude at the particular frequency may correspond to a measured magnitude at the particular frequency of a response provided by a cavity formed by closing the open-ended rectangular waveguide cavity using a materials standard including the conductive layer and the dielectric topcoat and having the known constitutive properties. Characteristics, such as resonant frequency and/or null magnitude, of the probe response measured using the probe calibration device 100 can be used to calibrate the probe by providing a relation between the characteristics and a sample having the conductive backing with the particular dielectric topcoat thickness and the constitutive properties.

The method 1000 may further include, at 1006, controlling a frequency (or an expected frequency) of a null of the electromagnetic energy returned by the probe and a magnitude of the electromagnetic energy returned by the probe at the frequency of the null based on dimensions of the cavity and/or based on a size of the aperture of the tuned pass element and a thickness of the first offset element, the second offset element, or both. Controlling, at 1006, may include configuring the calibration device with particular components. In some examples, controlling, at 1006, may be performed by configuring the calibration device with particular components before applying energy at 1002 and measuring electromagnetic energy at 1004. Additionally or alternatively, for example when multiple electromagnetic responses of the probe are measured as at 1008, controlling, at 1006, may include configuring the calibration device with particular components to measure each of the multiple responses using a differently configured calibration device.

As described, above, the calibration device may be configured with components dimensioned to provide a probe response that mimics a probe response measured when the probe is tested using a particular materials standard having a particular conductive material backing and a dielectric topcoat and known constitutive properties (e.g., known conductivity). For example, as described above, dimensions of the tuned pass element, the first offset element, the second offset element, the cavity, or a combination thereof, may be selected to control properties of an electromagnetic response measured by a probe (e.g., a probe response), such as the open-ended waveguide probe 300 illustrated in FIG. 3, when the probe calibration device 100 is coupled to the probe. The dimensions may include thicknesses of the first offset element, the tuned pass element, the second offset element, the backing element, or a combination thereof. The dimensions may also or alternatively include a shape or geometry of the second aperture 107 and/or a cross-sectional area of the second aperture 107. The properties of the electromagnetic response may include a frequency of a null (e.g., corresponding to a resonant frequency) or a magnitude of the response at the resonant frequency. Thus, to calibrate an open-ended waveguide to a particular materials standard, a probe calibration device having components (e.g., the first offset element, the tuned pass element, and/or the second offset element) configured to mimic the particular materials standard may be selected or assembled.

Measuring the electromagnetic energy returned by the probe in response to application of the energy to the probe may include measuring, at 1008, multiple electromagnetic responses of the calibration device. Each response of the multiple electromagnetic responses may be measured using a calibration device configured with one or more different components. In these examples, controlling, at 1006, may include configuring the calibration device with the one or more different components such that each of the multiple electromagnetic responses is measured using a differently configured calibration device. In some examples, each response of the multiple electromagnetic responses may be measured using a calibration device configured with a different thickness of the first offset element 104 of FIGS. 1 and 2, a differently sized second aperture 107, a different thickness of the second offset element 108, using a different probe calibration device including different dimensions, or a combination thereof.

For example, a first measurement of the multiple electromagnetic responses may be made by configuring the probe calibration device 100 of FIGS. 1 and 2 with a first configuration of components. The first configuration of components may correspond to the probe calibration device 100 being configured with the first offset element 104 and the second offset element 108 having first and second thicknesses, respectively, and with a tuned pass element 106 having a second aperture 107 that has a first cross-sectional area. The probe calibration device 100 of FIGS. 1 and 2 configured with the first configuration of components may be coupled to the probe 300 of FIG. 3 as described above. Energy may be applied to the probe across a band of frequencies. The first measurement may be made by measuring electromagnetic energy returned by the probe 300 when the probe 300 is coupled to the probe calibration device 100 configured with the first configuration of components. The first measurement may include a null at a first frequency and may include a particular magnitude at the first frequency. The first frequency and the particular magnitude at the first frequency may correspond to a frequency and magnitude of a probe response that would be measured by the probe 300 in response to application of the energy when the probe 300 is coupled to a first materials standard having a first conductive layer coated with a first dielectric material having a first thickness and having first constitutive properties.

A second measurement of the multiple electromagnetic responses may be made by configuring the probe calibration device 100 of FIGS. 1 and 2 (or another probe calibration device) with a second configuration of components. For example, the second configuration of components may correspond to the probe calibration device 100 being configured with the first offset element 104 and the second offset element 108 having third and fourth thicknesses, respectively, and with a tuned pass element 106 having a second aperture 107 that has a second cross-sectional area. At least one of the third thickness, the fourth thickness, or the second cross-sectional area is different than the first thickness, the second thickness, or the first cross-sectional area, respectively. The probe calibration device 100 of FIGS. 1 and 2 configured with the second configuration of components may be coupled to the probe 300 of FIG. 3 as described above. Energy may be applied to the probe across a band of frequencies. The second measurement may be made by measuring electromagnetic energy returned by the probe 300 when the probe 300 is coupled to the probe calibration device 100 (or the different probe calibration device) configured with the second configuration of components. The second measurement may include a null at a second frequency and may include a particular magnitude at the second frequency. The second frequency and the particular magnitude at the second frequency may correspond to a frequency and magnitude of a probe response that would be measured by the probe 300 in response to application of the energy when the probe 300 is coupled to a second materials standard having a second conductive layer coated with a second dielectric material having a second thickness and having second constitutive properties. The second conductive layer may be formed of or include a different conductive material than the first conductive layer. Alternatively or additionally, the second dielectric material may be different than the first dielectric material. Additionally or alternatively, the second thickness may be different than the first thickness.

A third measurement of the multiple electromagnetic responses may be made by configuring the probe calibration device 100 of FIGS. 1 and 2 (or another probe calibration device) with a third configuration of components. For example, the third configuration of components may correspond to the probe calibration device 100 being configured with the first offset element 104 and the second offset element 108 having fifth and sixth thicknesses, respectively, and with a tuned pass element 106 having a second aperture 107 that has a third cross-sectional area. At least one of the fifth thickness, the sixth thickness, or the third cross-sectional area is different than the first thickness, the second thickness, or the first cross-sectional area, respectively. Additionally or alternatively, at least one of the fifth thickness, the sixth thickness, or the third cross-sectional area is different than the third thickness, the fourth thickness, or the second cross-sectional area, respectively. The probe calibration device 100 of FIGS. 1 and 2 (or the different probe calibration device) configured with the third configuration of components may be coupled to the probe 300 of FIG. 3 as described above. Energy may be applied to the probe 300 across a band of frequencies. The third measurement may be made by measuring electromagnetic energy returned by the probe when the probe 300 is coupled to the probe calibration device 100 (or the different probe calibration device) configured with the third configuration of components. The third measurement may include a null at a third frequency and may include a particular magnitude at the third frequency. The third frequency and the particular magnitude at the third frequency may correspond to a frequency and magnitude of a probe response that would be measured by the probe 300 in response to application of the energy when the probe 300 is coupled to a third materials standard having a third conductive layer coated with a third dielectric material having a third thickness and having third constitutive properties. The third conductive layer may be formed of or include a different conductive material than the first conductive layer or the second conductive layer. Alternatively or additionally, the third dielectric material may be different than the first dielectric material or the second dielectric material. Additionally or alternatively, the third thickness may be different than the first thickness or the second thickness.

Thus, the method 1000 of FIG. 10 may include measuring probe responses using differently configured probe calibration devices, and the different probe responses may correspond to probe responses that may be measured using different materials standards. The method 1000 may include calibrating the probe by determining a relationship between probe measurements made using the probe calibration device 100 of FIG. 1 and constitutive properties (e.g., conductivity) of samples the probe calibration device 100 is configured to mimic. For example, the method 1000 may include determining a relationship between the first constitutive properties (e.g., a first conductivity) and the first measurements (e.g., the first frequency and the particular magnitude of the first frequency), a relationship between the second constitutive properties (e.g., a second conductivity) and the second measurements (e.g., the second frequency and the particular magnitude of the second frequency), and a relationship between the constitutive properties (e.g., a third conductivity) and the third measurements (e.g., the third frequency and the particular magnitude of the third frequency). In some examples, determining the relationships may include determining, at 1010, a best fit for the multiple measurements. For example, a best fit may be determined for the first measurement, the second measurement, and the third measurement according to any known or conventional statistical fitting technique. The best fit results may be used to calibrate the probe (or results of the probe) using any known calibration techniques.

Figure 11:
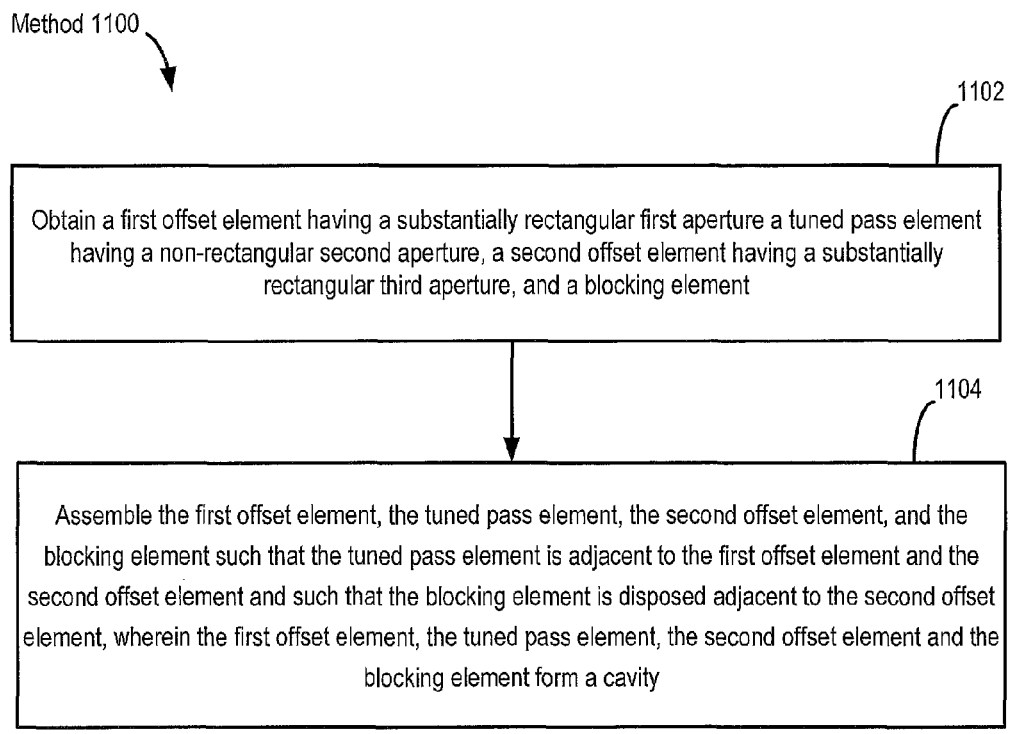
FIG. 11 is a flow chart of a method of fabricating the probe calibration device of FIGS. 1-3.

Referring to FIG. 11, a flow chart of a particular embodiment of a method 1100 of obtaining a probe calibration device is generally depicted. The method 1100 includes, at 1102, obtaining (e.g., fabricating or receiving) a first offset element having a substantially rectangular first aperture, obtaining a tuned pass element including a non-rectangular second aperture, obtaining a second offset element having a substantially rectangular third aperture, and obtaining a backing element. The first offset element may correspond to the first offset element 104 of FIGS. 1 and 4 and the first aperture may correspond to the first aperture 105. The tuned pass element may correspond to the tuned pass element 106 of FIGS. 1 and 6 and the second aperture may correspond to the second aperture 107. The second offset element may correspond to the second offset element 108 of FIGS. 1 and 5 and the third aperture may correspond to the third aperture 109. The backing element may correspond to the backing element 112 of FIGS. 1 and 7.

As described above, one or more of the tuned pass element 106, the first offset element 104, the second offset element 108, or the backing element 112 may be formed of or include metal. In some examples, the tuned pass element 106, the first offset element 104, the second offset element 108, or the backing element 112 may be fabricated as separate elements using any known fabrication technique. Alternatively or additionally, in other examples, one or more of the tuned pass element 106, the first offset element 104, the second offset element 108, or the backing element 112 may be formed as portions of a single fabrication element. For example, in some implementations, the first offset element 104, the tuned pass element 106, and the second offset element 108 may be formed from a single workpiece using an electrical discharge machining (EDM) technique to remove material from the workpiece at locations corresponding to the first aperture 105, the second aperture 107, and the third aperture 109. Thus, one or more of the tuned pass element 106, the first offset element 104, the second offset element 108, or the backing element 112 may be formed of or include metal and may be fabricated onto a single workpiece.

The method 1100 includes, at 1104, assembling the first offset element 104 of FIG. 1, the tuned pass element 106, the second offset element 108, and the backing element 112 such that the tuned pass element 106 is adjacent to the first offset element 104 and to the second offset element 108 and such that the backing element 112 is disposed adjacent to the second offset element 108. The first offset element 104, the tuned pass element 106, the second offset element 108 and the backing element 112 may form a cavity. For example, when assembled, the first offset element 104, the tuned pass element 106, the second offset element 108 and the backing element 112 may form the cavity 900 of FIGS. 9A and 9B. When assembled, the first offset element 104, the tuned pass element 106, the second offset element 108 and the backing element 112 may cooperate to provide particular electromagnetic responses for use in calibrating a probe as described above with reference to FIGS. 1-10.

Examples described above illustrate but do not limit the disclosure. It should also be understood that numerous modifications and variations are possible in accordance with the principles of the present disclosure. Accordingly, the scope of the disclosure is defined by the following claims and their equivalents.

The illustrations of the examples described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than shown in the figures or one or more method steps may be omitted. Accordingly, the disclosure and the figures are to be regarded as illustrative rather than restrictive.

Moreover, although specific examples have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. As the following claims reflect, the claimed subject matter may be directed to less than all of the features of any of the disclosed examples.

What is claimed is:

1. A probe calibration device comprising:
   a first offset element having a substantially rectangular first aperture;
   a tuned pass element distinct from the first offset element and disposed adjacent to the first offset element, the tuned pass element including a non-rectangular second aperture;
   a second offset element distinct from the tuned pass element and disposed adjacent to the tuned pass element and on a side opposite the first offset element, the second offset element having a substantially rectangular third aperture; and
   a backing element disposed adjacent to the second offset element, wherein the first offset element, the tuned pass element, the second offset element and the backing element form a probe calibration cavity that is closed off by the backing element, the probe calibration cavity dimensioned to provide a target electromagnetic response.

2. The probe calibration device of claim 1, wherein a cross-sectional shape of the first aperture has substantially same dimensions as a cross-sectional shape of the third aperture.

3. The probe calibration device of claim 1, wherein the first offset element and the second offset element have different thicknesses.

4. The probe calibration device of claim 1, wherein a shape of the second aperture corresponds to two overlapping congruent right triangles.

5. The probe calibration device of claim 1, wherein a first edge of the second aperture is aligned with a first edge of the first aperture, and wherein the first edge of the second aperture is aligned with a first edge of the third aperture.

6. The probe calibration device of claim 1, wherein at least one of the first offset element, the tuned pass element, the second offset element, or the backing element includes metal.

7. The probe calibration device of claim 1, further comprising:
   a guide section configured to align the first offset element, the tuned pass element, the second offset element, and the backing element;
   a first outer body section; and
   a second outer body section configured to couple to the first outer body section, wherein the first outer body section and the second outer body section, when coupled, at least partially enclose the guide section, the first offset element, the tuned pass element, and the second offset element.

8. The probe calibration device of claim 7, wherein the first outer body section is dimensioned and configured to receive the guide section.

9. The probe calibration device of claim 7, wherein the guide section includes a slot along an interior surface, wherein the first offset element includes a protrusion along an outer surface, wherein the tuned pass element includes a protrusion along an outer surface, wherein the second offset element includes a protrusion along an outer surface, wherein the backing element includes a protrusion along an outer surface, and wherein the protrusions of the first offset element, the tuned pass element, the second offset element, and the backing element intersect and are dimensioned and configured to fit into the slot of the guide section.

10. A method of calibrating a probe, the method comprising:
   applying energy to a probe coupled to a calibration device, the calibration device comprising:
      a first offset element having a substantially rectangular first aperture;

a tuned pass element distinct from the first offset element and disposed adjacent to the first offset element, the tuned pass element including a non-rectangular second aperture;

a second offset element distinct from the tuned pass element and disposed adjacent to the tuned pass element and on a side opposite the first offset element, the second offset element having a substantially rectangular third aperture; and a backing element disposed adjacent to the second offset element, wherein the first offset element, the tuned pass element, the second offset element and the backing element form a cavity; and measuring electromagnetic energy returned by the probe in response to application of the energy to the probe when the probe is coupled to the calibration device.

11. The method of claim 10, further comprising controlling a frequency of a null of the electromagnetic energy returned by the probe and a magnitude of the electromagnetic energy returned by the probe at the frequency of the null based on dimensions of the cavity.

12. The method of claim 10, further comprising controlling a frequency of a null of the electromagnetic energy returned by the probe and a magnitude of the electromagnetic energy returned by the probe at the frequency of the null based on a size of the second aperture of the tuned pass element and based on a thickness of the first offset element, the second offset element, or both.

13. The method of claim 10, wherein measuring the electromagnetic energy returned by the probe comprises measuring a plurality of electromagnetic responses of the probe when the probe is coupled to the calibration device, wherein each of the plurality of electromagnetic responses is measured using a different thickness of the first offset element, a different size of the second aperture of the tuned pass element, a different thickness of the second offset element, or a combination thereof.

14. A method of manufacturing a calibration device, the method comprising:
obtaining:
a first offset element having a substantially rectangular first aperture;
a tuned pass element distinct from the first offset element and including a non-rectangular second aperture;
a second offset element distinct from the tuned pass element and having a substantially rectangular third aperture; and
a backing element; and
assembling the first offset element, the tuned pass element, the second offset element, and the backing element such that the tuned pass element is adjacent to the first offset element and the second offset element and such that the backing element is disposed adjacent to the second offset element, wherein the first offset element, the tuned pass element, the second offset element and the backing element form a probe calibration cavity that is closed off by the backing element, the probe calibration cavity dimensioned to provide a target electromagnetic response.

15. The method of claim 14, wherein a cross-sectional shape of the first aperture has substantially same dimensions as a cross-sectional shape of the second aperture.

16. The method of claim 14, wherein edges of the first aperture and edges of the second aperture are aligned.

17. The method of claim 14, wherein the first offset element and the second offset element have different thicknesses.

18. The method of claim 14, wherein the first offset element, the tuned pass element, and the second offset element are fabricated using electrical discharge machining (EDM).

19. The method of claim 14, wherein at least one of the first offset element, the tuned pass element, the second offset element, or the backing element includes metal.

20. The method of claim 14, where the first offset element, the tuned pass element, the second offset element, and the backing element are formed of metal.

* * * * *